United States Patent
Fushimi

(10) Patent No.: US 9,655,204 B2
(45) Date of Patent: May 16, 2017

(54) LIGHTING SYSTEM, ADAPTER FOR WIRING TOOL, AND LIFE SUPPORT SYSTEM

(71) Applicant: Panasonic Intellectual Property Management Co., Ltd., Osaka (JP)

(72) Inventor: Shigemi Fushimi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/642,578

(22) Filed: Mar. 9, 2015

(65) Prior Publication Data

US 2015/0282278 A1    Oct. 1, 2015

(30) Foreign Application Priority Data

Mar. 25, 2014    (JP) ................. 2014-062362

(51) Int. Cl.
*H05B 37/02* (2006.01)
*H05B 37/03* (2006.01)
*A61F 9/08* (2006.01)

(52) U.S. Cl.
CPC .......... *H05B 37/0218* (2013.01); *A61F 9/08* (2013.01); *H05B 37/0272* (2013.01); *H05B 37/034* (2013.01); *Y02B 20/46* (2013.01)

(58) Field of Classification Search
CPC ............ H05B 37/0272; H05B 37/0227; H05B 37/0218; H05B 37/0245; H05B 37/0281; H05B 33/0854; H05B 37/0263; H05B 33/0845; H05B 37/029; H05B 33/0803; H05B 33/0815; H05B 33/0851; H05B 33/086

See application file for complete search history.

(56) References Cited

U.S. PATENT DOCUMENTS

2012/0026726 A1* 2/2012 Recker ................ F21K 9/13
362/157

FOREIGN PATENT DOCUMENTS

JP    2003-243189 A    8/2003

* cited by examiner

*Primary Examiner* — Monica C King
(74) *Attorney, Agent, or Firm* — Renner, Otto, Boisselle & Sklar, LLP

(57) ABSTRACT

An adapter includes a detection unit configured to detect an operating state of an illumination fixture, a communication unit configured to communicate with an analysis device, and a control unit configured to cause the communication unit to transmit a detection result of the detection unit to the analysis device. A lighting system includes a plurality of illumination devices. A life support system includes the plurality of illumination devices, and the analysis device configured to analyze behavior of a person. The plurality of illumination devices each include the adapter.

2 Claims, 7 Drawing Sheets

LIGHTING SYSTEM, ADAPTER FOR WIRING TOOL, AND LIFE SUPPORT SYSTEM

CROSS-REFERENCE TO RELATED APPLICATION

This application claims the benefit of priority of Japanese Patent Application Number 2014-062362, filed on Mar. 25, 2014, the entire contents of which are hereby incorporated by reference.

TECHNICAL FIELD

This disclosure generally relates to a lighting system, an adapter for wiring tool, and a life support system, and specifically relates to a lighting system including a plurality of illumination devices, an adapter for wiring tool that constitutes the illumination device together with an illumination fixture, and a life support system, using the lighting system, for supporting the life of a person.

BACKGROUND ART

A lighting system described in JP 2003-243189 A (hereinafter referred to as "Document 1") is illustrated as a conventional example. This conventional example includes illumination fixtures that are installed in rooms of a house, a remote controller, a main controller, and a gateway server.

Each illumination fixture includes a communication unit configured to perform wireless communication, a sensor unit configured to detect a human body, brightness, or the like, a light source unit such as a fluorescent light, and a control unit. A person lives normally in this house, and when the person enters the area inside the front door (hereinafter, referred to as the inner entrance) in which a fourth illumination fixture is installed, for example, a sensor unit of the fourth illumination fixture detects the person, and a light source unit is turned on. When the person moves from the inner entrance to a living room where a second illumination fixture and a third illumination fixture are installed, sensor units of the third illumination fixture and then the second illumination fixture detect the person, and the third illumination fixture and the second illumination fixture turn on respective light source units.

Also, in this conventional example, an operating situation (lighted, unlighted) of each of the illumination fixtures, a detection result of the sensor unit, and the like are transmitted from the communication unit to the gateway server. The gateway server stores information such as operating situations and detection results that is transmitted from the illumination fixtures, and determines whether an abnormality (immobilized due to illness, or the like) has occurred in the person based on the stored information. The gateway server is configured to, upon determining that an abnormality has occurred, notify the occurrence of the abnormality to a pre-registered address (e-mail address, or the like).

Incidentally, the conventional example described in Document 1 requires a dedicated illumination fixture having a wireless communication function, rather a general illumination fixture. Accordingly, with the lighting system described in Document 1, there is a problem in that widespread adoption is difficult due to high implementation costs (initial costs).

SUMMARY OF THE INVENTION

The present technology has been made in view of the above-described problems, and an object of the present technology is to reduce implementation costs.

A lighting system according to an aspect of the present invention includes: a plurality of illumination devices arranged in a living space; and an analysis device configured to analyze behavior of a person who lives in the living space. Each of the plurality of illumination devices includes: an illumination fixture; and an adapter for wiring tool. The illumination fixture includes: a light source; a lighting device configured to turn on the light source; a fixture body supporting the light source and the lighting device; and a connection unit connected to the adapter. The adapter includes: a detection unit configured to detect an operating state of the illumination fixture; a communication unit configured to communicate with the analysis device; and a control unit configured to cause the communication unit to transmit a detection result of the detection unit to the analysis device.

An adapter for wiring tool according to another aspect of the present invention is configured to be detachably connected to a wiring tool that is installed in a living space electrically and mechanically, and to be detachably coupled to a connection unit included in an illumination fixture. The adapter includes: a detection unit configured to detect an operating state of the illumination fixture; a communication unit configured to communicate with an analysis device, and a control unit configured to cause the communication unit to transmit a detection result of the detection unit to the analysis device.

A life support system according to yet another aspect of the present invention includes: a plurality of illumination devices arranged in a living space; and an analysis device configured to analyze behavior of a person who lives in the living space. Each of the plurality of illumination devices includes: an illumination fixture; and an adapter for wiring tool. The illumination fixture includes: a light source; a lighting device configured to turn on the light source; a fixture body supporting the light source and the lighting device; and a connection unit connected to the adapter. The adapter includes: a detection unit configured to detect an operating state of the illumination fixture; a communication unit configured to communicate with the analysis device; and a control unit configured to cause the communication unit to transmit a detection result of the detection unit to the analysis device. The analysis device is configured to derive a lifestyle pattern of the person by analyzing the detection result received from the adapter, and to store a typical lifestyle pattern and determine a well-being of the person by comparing the typical lifestyle pattern with the lifestyle pattern derived from analysis of the detection result.

BRIEF DESCRIPTION OF THE DRAWINGS

The figures depict one or more implementations in accordance with the present teaching, by way of example only, not by way of limitations. In the figures, like reference numerals refer to the same or similar elements.

DETAILED DESCRIPTION

Embodiment 1

Figure 1:
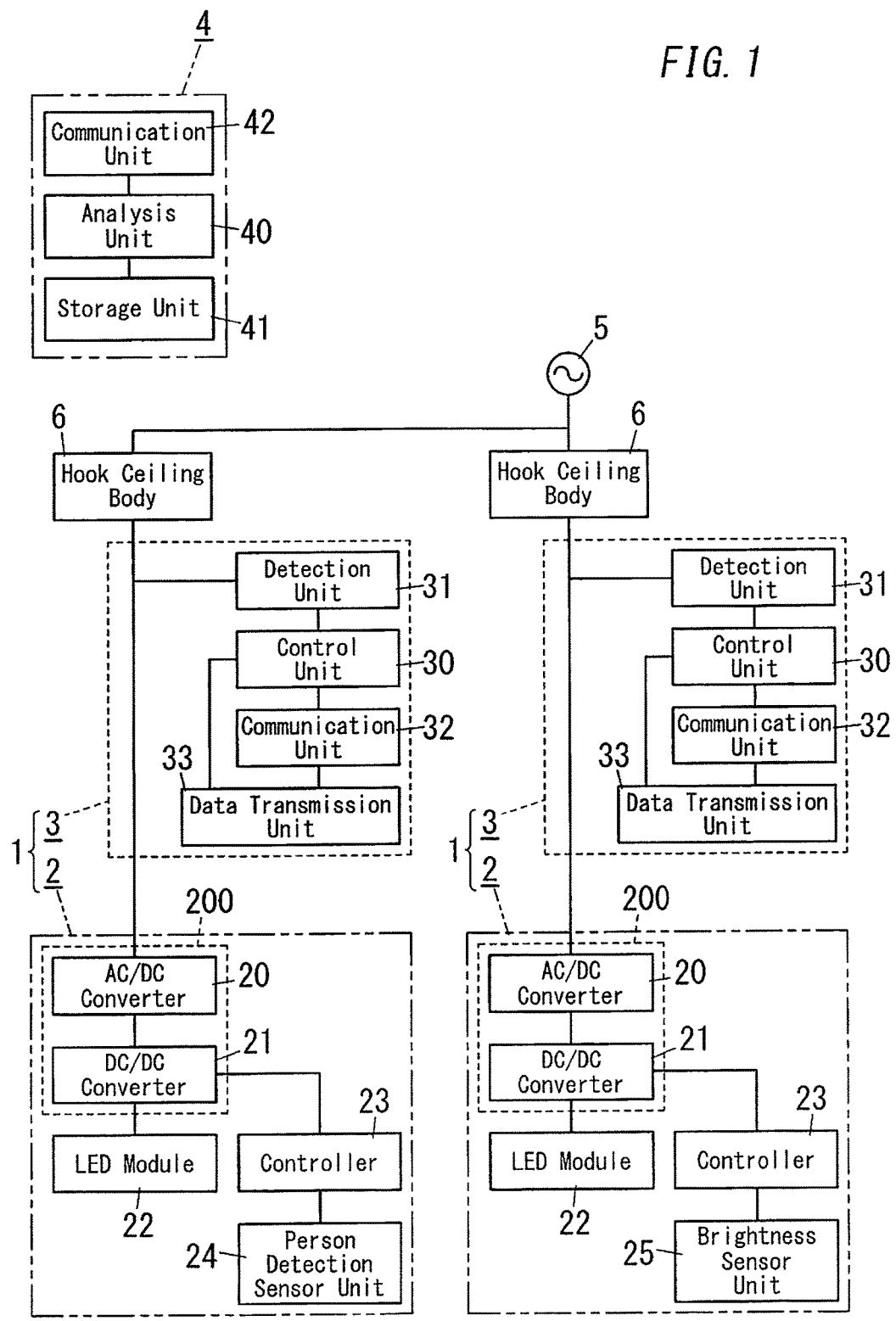
FIG. 1 is a system configuration diagram illustrating a lighting system and a life support system according to Embodiment 1.

A lighting system and a life support system according to Embodiment 1 include, as shown in FIG. 1, a plurality of (two in the diagram) illumination devices 1 that are arranged in a living space, and an analysis device 4 configured to analyze behavior of a person who lives in the living space.

Each illumination device 1 includes an illumination fixture 2 and an adapter for wiring tool (hook ceiling rosette) 3 (hereinafter abbreviated to an adapter).

The adapter 3 is detachably connected to a hook ceiling body 6, which is one of wiring tools that are installed in the living space (ceilings of rooms in a residence, for example), electrically and mechanically. The hook ceiling body 6 constitutes a hook ceiling rosette with a hook ceiling connector. The adapter 3 includes, as shown in FIG. 1, a control unit 30, a detection unit 31, and a communication unit 32. Also, the adapter 3 may include a data transmission unit 33.

The detection unit 31 is configured to detect the operating state of the illumination fixture 2. Specifically, the detection unit 31 measures the magnitude of current (load current) that is supplied from a commercial AC power supply 5 to the illumination fixture 2 via the hook ceiling body 6, and detects the operating state of the illumination fixture 2 by comparing the measurement value with a predetermined threshold value. That is, in the case where the illumination fixture 2 is in a lighted state, since the measurement value of the load current exceeds the threshold value, the detection unit 31 can detect that the illumination fixture 2 is in a lighted state. Also, in the case where the illumination fixture 2 is in an unlighted state, since the measurement value of the load current is the threshold value or less, the detection unit 31 can detect that the illumination fixture 2 is in an unlighted state. Also, the detection unit 31 is configured to output a detection result of the operating state of the illumination fixture 2 to the control unit 30. Note that the detection unit 31 preferably measures the load current using a current sensor, for example. Furthermore, it is preferable that the detection unit 31 compares the measurement value of the load current with the threshold value using a comparator, and outputs, to the control unit 30, a detection signal (detection result) that is at a high level when in a lighted state, and is at a low level when in an unlighted state. Note that the detection unit 31 may output, to the control unit 30, a detection signal that is at a low level when in a lighted state, and is at a high level when in an unlighted state. That is, the detection unit 31 may output, to the control unit 30, a detection signal, the level of which differs when in a lighted state and when in an unlighted state.

The communication unit 32 is configured to communicate (perform wireless communication using radio waves as a communication medium, for example) with the analysis device 4.

The data transmission unit 33 is configured to perform data transmission with a controller 23, which will be described later, of the illumination fixture 2 using a short-range wireless communication system that is standardized in IEEE 802.15.1, or a wired communication system such as a UART (Universal Asynchronous Receiver Transmitter), for example.

The control unit 30 includes a microcontroller. The control unit 30 stores a detection signal (hereinafter referred to as detection data) that is outputted from the detection unit 31 in a memory embedded in the microcontroller. Also, the control unit 30 stores data (described later) that the data transmission unit 33 receives from the controller 23 of the illumination fixture 2 in the memory. The control unit 30 causes the communication unit 32 to transmit detection data or the like stored in the memory to the analysis device 4.

Figure 2A:
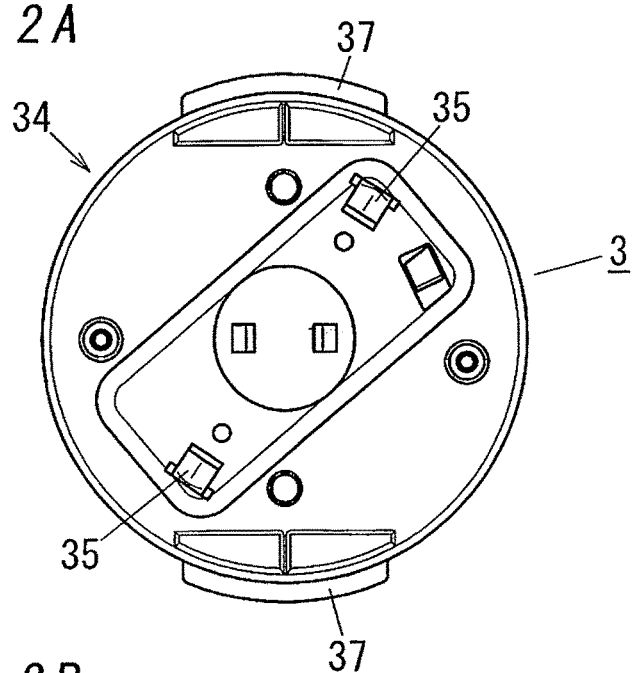
FIG. 2A is a top view of an adapter according to Embodiment 1.
Figure 2B:
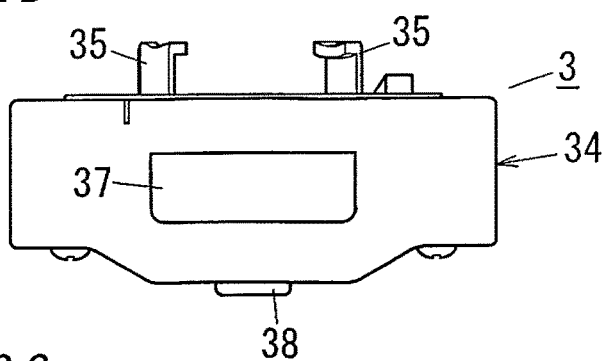
FIG. 2B is a side view of the adapter according to Embodiment 1.
Figure 2C:
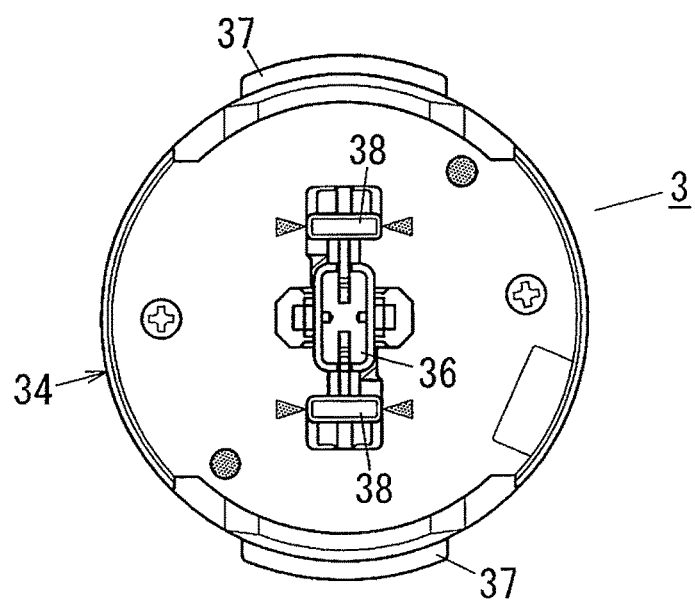
FIG. 2C is a bottom view of the adapter according to Embodiment 1.

The appearance of the adapter 3 is shown in FIGS. 2A to 2C. The adapter 3 includes, as shown in FIGS. 2A to 2C, a container 34, a pair of hook blades 35, a receptacle connector 36, a pair of hook members 37, a pair of operation members 38, and the like.

The container 34 is formed in a flat cylindrical shape by an insulating material such as a synthetic resin. The pair of hook blades 35 is provided so as to protrude upward from an upper face of the container 34. The pair of hook blades 35 is to be detachably connected to a known hook ceiling body 6 (refer to FIG. 1) electrically and mechanically.

The receptacle connector 36 is provided so as to be exposed in the center of a lower face of the container 34. The receptacle connector 36 is electrically connected, inside the container 34, to the pair of hook blades 35.

The pair of hook members 37 retractably protrudes from a side face of the container 34, and is pressed outward from the side face of the container 34 by a spring that is housed inside the container 34. The operation members 38 are coupled, inside the container 34, to the respective hook members 37, and a portion of the operation members 38 is exposed from the lower face of the container 34. That is, when the pair of operation members 38 is operated by being pressed outwardly, the hook members 37 that are coupled to the respective operation members 38 can be retracted inside the container 34.

The illumination fixture 2 includes, as shown in FIG. 1, an AC/DC converter 20, a DC/DC converter 21, and an LED module 22. The illumination fixture 2 may further include the controller 23. Furthermore, the illumination fixture 2 may include at least one of a person detection sensor unit 24 and a brightness sensor unit 25.

The AC/DC converter 20 is configured to convert an AC voltage/AC current that is supplied from the AC power supply 5 via the hook ceiling body 6 and the adapter 3 to a DC voltage/DC current. The DC/DC converter 21 is configured to convert (lower, for example) the DC voltage outputted from the AC/DC converter 20 to a desired DC voltage.

The LED module 22 is configured by a plurality of LEDs (light emitting diodes) that are mounted on a substrate. That is, the LED module 22 is a light source of the illumination fixture 2. Note that the light source is not limited to the LED module 22, and may be an organic electroluminescence element, a fluorescent lamp, an incandescent lamp, or the like.

The person detection sensor unit 24 is configured to detect the presence of a person in a detection region, and output a person detection signal (person detection result) indicating that the presence of a person is detected to the controller 23. Such a person detection sensor unit 24 is configured to sense heat rays (infrared light) that are radiated from the human body by a pyroelectric element, for example. Note that the person detection sensor unit 24 is not limited to a passive type sensor using the pyroelectric element, and may be configured by an active type sensor using ultrasonic waves or radio waves.

The brightness sensor unit 25 is configured to measure ambient brightness (illuminance), and output a measurement value of the brightness to the controller 23. Such a brightness sensor unit 25 is configured to measure the brightness using a photoelectric conversion element such as a solar cell, a photodiode, or a phototransistor.

The controller 23 includes a microcontroller. The controller 23 is configured to control the DC/DC converter 21 based on the person detection signal that is received from the person detection sensor unit 24 and the measurement value that is received from the brightness sensor unit 25. For example, if the measurement value of brightness is a predetermined threshold value or more, the controller 23 preferably stops the DC/DC converter 21 and turns off the LED module 22. Also, in the case where the measurement value of brightness is less than the threshold value, the controller 23 preferably feedback-controls the output of the DC/DC converter 21 such that the measurement value matches a pre-set target value of brightness. Alternatively, the controller 23 preferably causes the DC/DC converter 21 to operate and turn on the LED module 22, in the case of having received the person detection signal, and stops the DC/DC converter 21 and turns off the LED module, in the case of not receiving the person detection signal. As a result of the controller 23 performing the above control operations, energy saving can be realized by preventing the LED module 22 from being turned on unnecessarily.

Figure 3:
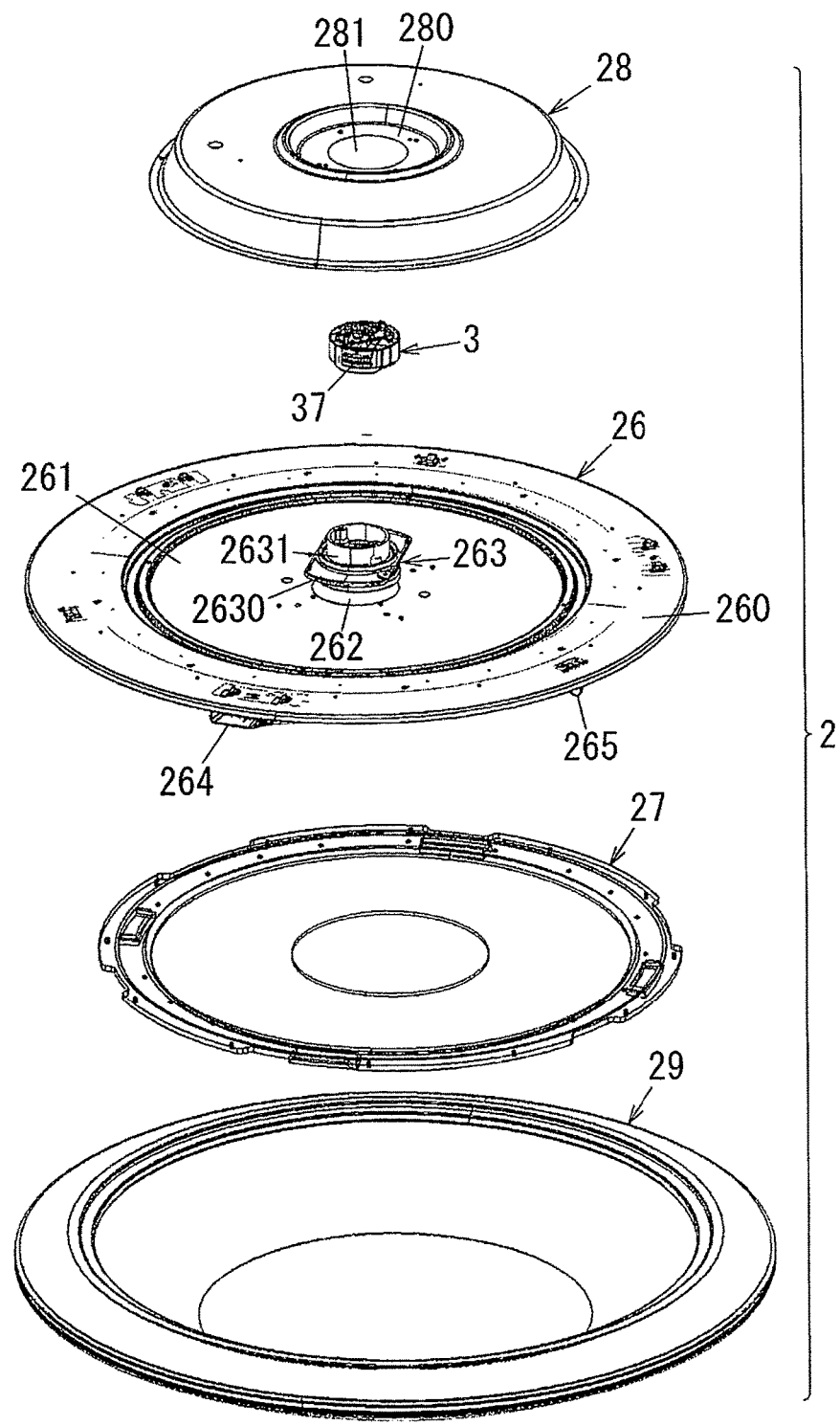
FIG. 3 is an exploded perspective view of an illumination fixture in Embodiment 1.

FIG. 3 shows an exploded perspective view of the illumination fixture 2. The illumination fixture 2 includes a fixture body 26, a light guide body 27, a body cover 28, a cover 29, and the like. The fixture body 26 is integrally formed, with a metal plate such as a steel plate, by a base portion 260, which is shaped like a ring, and a projecting base portion 261, which is shaped like a dish and is provided inside the base portion 260. A circular through hole 262 passes through the projecting base portion 261 at the center thereof. A holder 263 (connection unit) is attached to the through hole 262. Note that the LED module 22 is attached to a lower face of the base portion 260.

The holder 263 is integrally formed, with a synthetic resin material, by an elliptical flange portion 2630 and a cylindrical insertion portion 2631, which passes through the flange portion 2630 at the center thereof. A portion of the insertion portion 2631 that is lower than the flange portion 2630 is inserted into the through hole 262, and the flange portion 2630 is fixed to the projecting base portion 261 by a screw, and as a result the holder 263 is attached to the fixture body 26.

A hook groove to which the pair of hook members 37 of the adapter 3 is to be caught is provided in an inner circumferential surface of the insertion portion 2631. That is, the adapter 3 is inserted into the insertion portion 2631 of the holder 263, the holder 263 and the adapter 3 are coupled by the pair of hook members 37 being caught in the hook groove, and as a result the fixture body 26 is attached to the adapter 3.

A lighting device 200 (AC/DC converter 20 and DC/DC converter 21) is attached on the projecting base portion 261 of the fixture body 26. The lighting device 200 includes a plug connector. As a result of the plug connector being connected to the receptacle connector 36 of the adapter 3, a power supply path from the AC power supply 5 to the lighting device 200 is formed.

Also, two or more fixtures 264 for detachably attaching the cover 29 and two or more support metal fittings 265 for supporting the cover 29 are provided alternately in a circumferential direction at equal intervals on a lower face of the base portion 260 of the fixture body 26. Note that since the fixture 264 and the support metal fitting 265 are conventionally known, detailed description will be omitted.

The body cover 28 is formed in a deep dish like shape by a metal plate, and is fixed to the fixture body 26 by a screw so as to cover the projecting base portion 261 of the fixture body 26 from above. A projecting portion 280 having a circular truncated cone shape is provided at the center of a bottom face of the body cover 28, and a circular through hole 281 passes through the projecting portion 280 at the center thereof. That is, the adapter 3 is inserted into the insertion portion 2631 of the holder 263 through the through hole 281 of the body cover 28.

The light guide body 27 is formed in a disk like shape by a synthetic resin material, such as acryl, having translucency. The light guide body 27 is attached to a lower face side of the fixture body 26, and is configured to emit light that is radiated from the LED module 22 downward while guiding the light toward the center.

The cover 29 is formed by a synthetic resin material, such as acryl, having translucency in a dome like shape in which an upper face is open, and is attached to the lower face side of the fixture body 26 with the fixtures 264 and the support metal fittings 265. Also, the cover 29 includes a diffusion structure that diffuses light that is emitted from the light guide body 27. Note that the diffusion structure is realized by a white coating film that is formed on a surface of the cover 29, a diffusion material that is mixed into a synthetic resin material that forms the cover 29, an asperity that is formed on the surface of the cover 29, or the like. Since the diffusion structure is provided in the cover 29, as described above, the uniformity of light that is radiated to an illumination space can be further improved. Note that it is preferable that the person detection sensor unit 24 and the brightness sensor unit 25 are attached to the flange portion 2630 of the fixture body 26.

Note that the above-described illumination fixture 2 is one example, and the shape and structure of the fixture body 26 is not limited to the above-described embodiment.

The analysis device 4 includes, as shown in FIG. 1, an analysis unit 40, a storage unit 41, and a communication unit 42. The analysis device 4 is configured by a general purpose computer system. The analysis unit 40 performs analysis processing by causing the computer system to execute software (program) for causing the computer system to perform various processing including the analysis processing. The storage unit 41 is configured by a high capacity storage device such as a hard disk drive. The communication unit 42 is configured to communicate (wirelessly communicate using radio waves as a communication medium, for example) with the communication unit 32 of the adapter 3.

Figure 4:
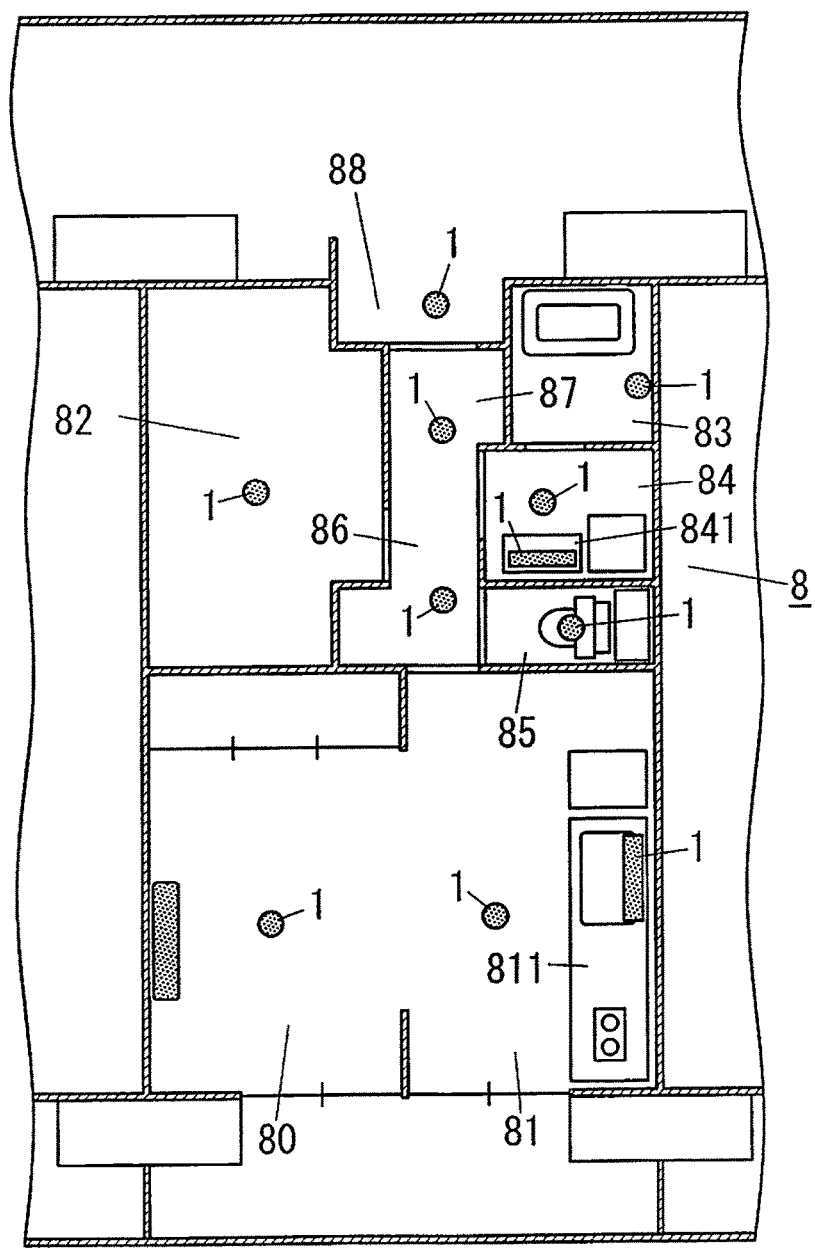
FIG. 4 is a floor plan of a house in which a plurality of illumination devices according to Embodiment 1 are installed.

A plurality of illumination devices 1 according to the present embodiment are installed in a detached house or a dwelling unit 8 of an apartment building, as shown in FIG. 4, for example. The rooms of the dwelling unit 8 include a living room 80, a kitchen 81, a bedroom 82, a bathroom 83, a washroom 84, and a lavatory 85, and the illumination device 1 is installed in each room. The illumination device 1 is also installed in a hallway 86, an inner entrance 87 and outer entrance (that is, the area outside the front door) 88, a washstand 841 in a washroom 84, and a sink 811 in a kitchen 81. Note that, in each of the living room 80, the kitchen 81, and the bedroom 82 in the dwelling unit 8 shown in FIG. 4, an illumination fixture 2 including the brightness sensor unit 25 is preferably installed as the illumination fixture 2 that is included in the illumination device 1. Also, in each of the rooms other than the living room 80, the kitchen 81, and the bedroom 82 in the dwelling unit 8 shown in FIG. 4, an illumination fixture 2 including the person detection sensor unit 24 is preferably installed as the illumination fixture 2 that is included in the illumination device 1.

While a dweller (person) of a dwelling unit 8 is at home, the illumination devices 1 (illumination fixtures 2) in respective rooms are appropriately turned on and off. In each illumination device 1, the adapter 3 detects an operating state (lighted state and unlighted state) of the illumination fixture 2, and notifies the detection result to the analysis device 4. Note that the hook ceiling body 6 is often not installed in the bathroom 83, the washroom 84, the lavatory 85, the hallway 86, the inner entrance 87, or the outer entrance 88. Accordingly, in each of the illumination devices 1 that are to be installed in these areas, the AC/DC converter 20 is, normally, directly connected to the AC power supply 5. Therefore, in each of these illumination devices 1, it is preferable that the controller 23 determines the operating state of the LED module 22, and causes a communication unit included in the illumination device 1 to transmit the detection result of the operating state to the analysis device 4.

The analysis device 4 is configured to receive a detection result that is notified from the adapter 3 of the illumination device 1 (or illumination device 1) by the communication unit 42, and store the received detection result in the storage unit 41. In the analysis device 4, a lifestyle pattern of a person can be derived by analyzing the detection result stored in the storage unit 41 with the analysis unit 40.

For example, the analysis unit 40 determines that the person has woken up when the illumination device 1 in the washroom 84 or the illumination device 1 in the lavatory 85 is switched to a lighted state in the morning, and stores the time in the storage unit 41 as the wake-up time on that day. Also, the analysis unit 40 determines that the person went to bed when all the illumination devices 1 are switched to an unlighted state, and stores the time in the storage unit 41 as the bedtime on that day. Furthermore, the analysis unit 40 stores the time of day, the number of times, and the duration of time per lighting that the illumination device 1 in the lavatory 85 was turned on during one day in the storage unit 41. Also, the analysis unit 40 stores the time of day and the lighting duration that the illumination device 1 in the bathroom 83 was turned on during one day in the storage unit 41.

It is preferable that the analysis unit 40 is configured to derive a lifestyle pattern of the person from data that is stored in the storage unit 41, including the wake-up time and bedtime, the number of times and the duration/amount of time that the lavatory was used per day, the amount of time taken for bathing or showering per day, and the like.

Figure 5A:
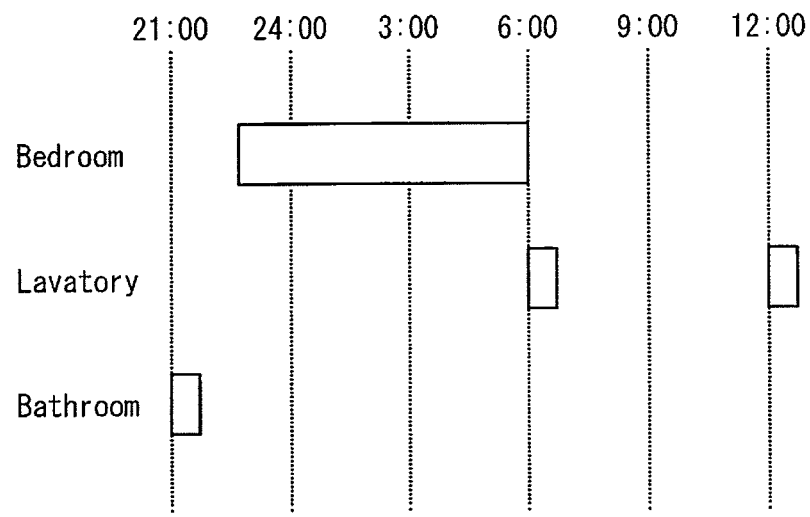
FIG. 5A is a diagram illustrating a typical lifestyle pattern in Embodiment 1.

Furthermore, it is preferable that the analysis unit 40 is configured to derive a typical lifestyle pattern of the person from an average value of the lifestyle patterns over a long period of time (one month to one year, for example). FIG. 5A shows an example of a typical lifestyle pattern. The lifestyle pattern of the person frequently involves taking a bath at approximately 21:00, going to bed at approximately 22:00, waking up at approximately 6:00, and using the lavatory just after waking up and around noon.

As described above, the lighting system according to the present embodiment includes a plurality of the illumination devices 1 arranged in a living space and the analysis device 4 configured to analyze the behavior of a person who lives in the living space. Each of the plurality of illumination devices 1 includes the illumination fixture 2 and the adapter 3 for wiring tool (hook ceiling rosette). The illumination fixture 2 includes the light source (LED module 22) and the lighting device 200 (AC/DC converter 20 and DC/DC converter 21) configured to turn on the light source. Also, the illumination fixture 2 includes the fixture body 26 that supports the light source and the lighting device 200, and the connection unit (holder 263) that is connected to the adapter 3. The adapter 3 includes the detection unit 31 configured to detect the operating state of the illumination fixture 2, the communication unit 32 configured to communicate with the analysis device 4, and the control unit 30 configured to cause the communication unit 32 to transmit the detection result of the detection unit 31 to the analysis device 4.

Since the lighting system according to the present embodiment is configured as described above, merely by changing an adapter to which an existing illumination fixture 2 is connected to the adapter 3 according to the present embodiment, the operating state of the illumination fixture 2 (illumination device 1) can be detected, and the detection result can be collected by the analysis device 4. As a result, the implementation costs of the lighting system according to the present embodiment can be reduced compared with the lighting system described in Document 1.

Also, the analysis device 4 of the present embodiment is preferably configured to derive a lifestyle pattern of the person by analyzing the detection result received from the adapter 3, as described above.

In the analysis device 4, the derivation accuracy can be easily improved by deriving the lifestyle pattern of the person from an operating state of an illumination fixture 2 (illumination device 1) that is used relatively frequently in the daily life of the person.

Also, the illumination fixture 2 in the present embodiment preferably includes the person detection sensor unit 24 configured to detect the presence of a person in a detection region, and the controller 23 configured to control the lighting device 200 (AC/DC converter 20 and DC/DC converter 21) in accordance with the person detection result of the person detection sensor unit 24. The control unit 30 of the adapter 3 is preferably configured to acquire the person detection result of the person detection sensor unit 24 from the controller 23, and cause the communication unit 32 to transmit the acquired person detection result to the analysis device 4. The analysis device 4 is preferably configured to derive a lifestyle pattern of the person by analyzing the detection result (operating state of illumination fixture 2) and the person detection result that are received from the adapter 3.

That is to say, the controller 23 of the illumination fixture 2 may transmit the measurement value of the brightness sensor unit 25 to the data transmission unit 33 of the adapter 3, or may directly transmit the person detection result of the person detection sensor unit 24 from the communication unit included in the illumination fixture 2 to the analysis device 4.

For example, the illumination device 1 including the person detection sensor unit 24 is configured to prevent the controller 23 from turning off the LED module 22 until a predetermined lighting holding time elapses after the person detection sensor unit 24 no longer detects a person. Accordingly, the derivation accuracy of a lifestyle pattern can be improved by the analysis device 4 estimating the use situation of the lavatory 85 from the person detection result of the person detection sensor unit 24, rather than by estimating the use situation of the lavatory 85 from the operating state of the illumination device 1 installed in the lavatory 85.

Also, the illumination fixture 2 in the present embodiment is preferably configured to include the brightness sensor unit 25 configured to measure the ambient brightness, and the controller 23 configured to control the lighting device 200 according to the measurement value of the brightness sensor unit 25. The control unit 30 of the adapter 3 is preferably configured to acquire the measurement value of the brightness sensor unit 25 from the controller 23, and cause the communication unit 32 to transmit the acquired measurement value to the analysis device 4. The analysis device 4 is preferably configured to derive a lifestyle pattern of the person by analyzing the detection result (operating state of illumination fixture 2) and the measurement value that are received from the adapter 3.

For example, the analysis device 4 can determine that a person has fallen asleep if the measurement value of brightness remains at a predetermined lower limit value or less until a predetermined time (10 minutes, for example) has elapsed after the time when the illumination device 1 installed in the bedroom 82 was turned off. Therefore, the accuracy of derivation of a lifestyle pattern of a person by the analysis device 4 can be improved, compared with a case where the behavior of the person is estimated from only an operating state of the illumination device 1.

It is preferable that the illumination fixture 2 in the present embodiment includes the brightness sensor unit 25 configured to measure the ambient brightness, and the controller 23 controls the lighting device 200 according to the person detection result by the person detection sensor unit 24 and the measurement value by the brightness sensor unit 25. The control unit 30 of the adapter 3 is preferably configured to acquire the measurement value of the brightness sensor unit 25 from the controller 23, and cause the communication unit 32 to transmit the acquired measurement value to the analysis device 4. The analysis device 4 is preferably configured to derive a lifestyle pattern of the person by analyzing the detection result (operating state of illumination fixture 2), the person detection result, and the measurement value that are received from the adapter 3.

The adapter 3 for wiring tool (hook ceiling) in the present embodiment is configured to be detachably connected to a wiring tool (hook ceiling body 6) that is installed in a living space electrically and mechanically, and to be detachably coupled to the connection unit (holder 263) included in the illumination fixture 2. The adapter 3 includes the detection unit 31 configured to detect the operating state of the illumination fixture 2, the communication unit 32 configured to communicate with the analysis device 4, and the control unit 30 configured to cause the communication unit 32 to transmit the detection result of the detection unit 31 to the analysis device 4.

The life support system according to the present embodiment includes a plurality of the illumination devices 1 that are arranged in a living space (dwelling unit 8), and the analysis device 4 configured to analyze the behavior of a person who lives in the living space. Each of the plurality of illumination device 1 includes the illumination fixture 2, and the adapter 3 for wiring tool (hook ceiling rosette). The illumination fixture 2 includes the light source (LED module 22), the lighting device 200 (AC/DC converter 20 and DC/DC converter 21) configured to turn on the light source, the fixture body 26 that supports the light source and the lighting device 200, and the connection unit (holder 263) to be connected to the adapter 3. The adapter 3 includes the detection unit 31 configured to detect the operating state of the illumination fixture 2, the communication unit 32 configured to communicate with the analysis device 4, and the control unit 30 configured to cause the communication unit 32 to transmit the detection result of the detection unit 31 to the analysis device 4. The analysis device 4 is configured to derive a lifestyle pattern of the person by analyzing the detection result received from the adapter 3. Furthermore, the analysis device 4 is preferably configured to store a typical lifestyle pattern, and determine the well-being of the person by comparing the lifestyle pattern derived by analyzing the detection result with the typical lifestyle pattern.

The life support system according to the present embodiment can detect the operating state of the illumination fixture 2 (illumination device 1) and collect the detection result by the analysis device 4, merely by changing the adapter to which the existing illumination fixture is connected to the adapter 3. As a result, the life support system according to the present embodiment has an effect of reducing the implementation costs compared with the lighting system described in Document 1.

Note that the adapter 3 is not limited to the adapter 3 according to the present embodiment, and can be formed in an arbitrary shape. The adapter 3 is not limited to an adapter for the hook ceiling, and can be configured so as to be connected to an arbitrary wiring tool. Furthermore, the adapter 3 can be connected to the illumination fixture 2. The illumination fixture 2 can also be configured so as to receive electric power supplied from the wiring tool via the adapter 3.

Figure 5B:
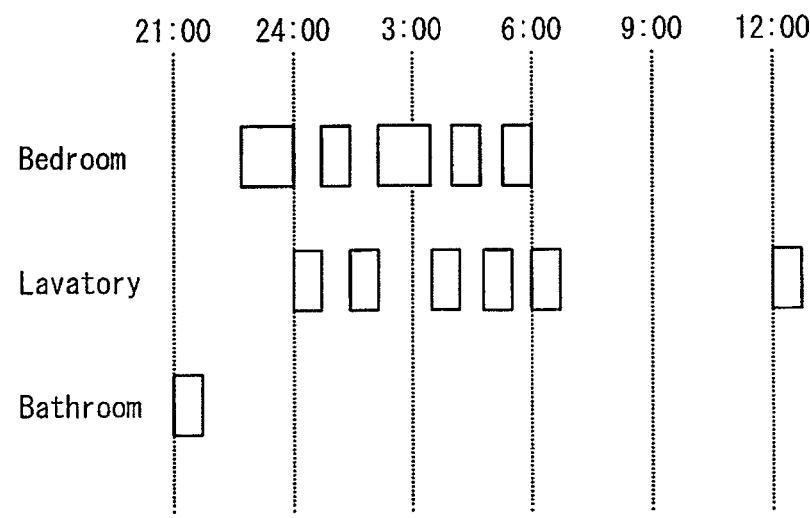
FIG. 5B is a diagram illustrating a lifestyle pattern when an abnormality occurs in Embodiment 1.

For example, FIG. 5A shows a typical lifestyle pattern, and FIG. 5B shows a lifestyle pattern derived by the analysis device 4 (analysis unit 40 thereof) on an arbitrary day. In the lifestyle pattern shown in FIG. 5B, the person is considered to have used the lavatory 85 many times after going to bed. The analysis device 4 (analysis unit 40 thereof) preferably determines that, by comparing the typical lifestyle pattern (refer to FIG. 5A) with the lifestyle pattern of the person (refer to FIG. 5B), the person is not well considering extremely large number of times that the lavatory was used during the night. Note that it is preferable that the evaluation criteria for the analysis device 4 (analysis unit 40 thereof) determining the well-being (presence of abnormality) of a person is set according to the age of the person and whether or not the person has a chronic disease.

Here, it is preferable that the analysis device 4 is configured to be able to perform communication via a wide area network (WAN) such as the Internet. The analysis device 4, upon determining that the person is not well, preferably notifies a pre-registered contact of the occurrence of an abnormality. Note that the contact may be an e-mail address of a relative of the person or an administrative organ, for example. Alternatively, in the case where a communication terminal that can communicate with the analysis device 4 is installed in a control room of the apartment building, the analysis device 4 preferably notifies the communication terminal of the occurrence of an abnormality.

Embodiment 2

A life support system according to Embodiment 2 will be described in detail with reference to drawings. Note that the life support system according to the present embodiment has a basic configuration in common with the life support system according to Embodiment 1. Accordingly, constituent elements in common with the life support system according to Embodiment 1 are provided with the same reference numerals, and description thereof will be omitted.

Figure 6:
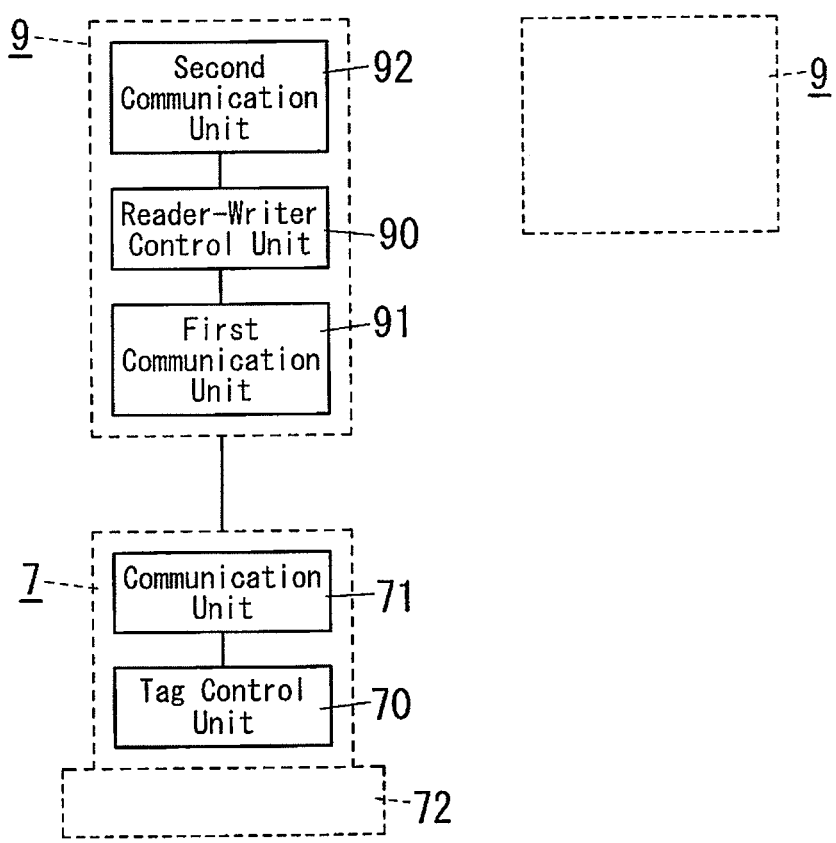
FIG. 6 is a block diagram of an identification tag and a plurality of reader-writers in a life support system according to Embodiment 2.

The life support system according to the present embodiment preferably includes, as shown in FIG. 6, an identification tag 7 to be attached to an apparatus 72 used by a person, and a plurality of reader-writers 9 that are arranged in a living space. The identification tag 7 preferably includes a communication unit 71 (transmission unit) configured to transmit a specific identification code to the plurality of reader-writers 9. The plurality of reader-writers 9 each is preferably configured to transmit, to the analysis device 4, the identification code that is received from the communication unit 71 of the identification tag 7. The analysis device 4 is preferably configured to derive a lifestyle pattern of the person by analyzing the detection result received from the adapter 3 and the identification code received from the plurality of reader-writers 9.

The identification tag 7, which is also referred to as a RF tag, includes a tag control unit 70 and the communication unit 71. Each of the reader-writers 9 includes a reader-writer control unit 90, a first communication unit 91, and a second communication unit 92, and the like. The identification tag 7 and the plurality of reader-writers 9 constitute a conventionally known RFID system.

The tag control unit 70 stores a specific identification code. The communication unit 71 of the identification tag 7 is configured to perform short-range wireless communication with the first communication unit 91 of a reader-writer 9, and supply electric power supplied from the reader-writer 9 to the tag control unit 70 with a contactless power transmission technology.

That is, upon the identification tag 7 entering an area where communication can be performed with the first communication unit 91 of a reader-writer 9, the communication unit 71 and the tag control unit 70 are activated by the electric power transmitted contactlessly from the reader-writer 9. Then, the tag control unit 70 causes the communication unit 71 to transmit the specific identification code to the reader-writer 9.

The reader-writer control unit 90 stores a specific ID. The reader-writer control unit 90, upon the first communication unit 91 receiving the identification code of the identification tag 7, generates a transmission frame including the identification code, its own ID, and the current time, and passes the transmission frame to the second communication unit 92. The second communication unit 92 transmits the transmission frame to the analysis device 4 by a radio signal.

In the analysis device 4, a communication unit 42 receives the radio signal, and passes the transmission frame included in the radio signal to an analysis unit 40. The analysis unit 40 associates the data of the identification code, the ID of the reader-writer 9, and the time that are included in the transmission frame, and stores the associated data in the storage unit 41.

Figure 7:
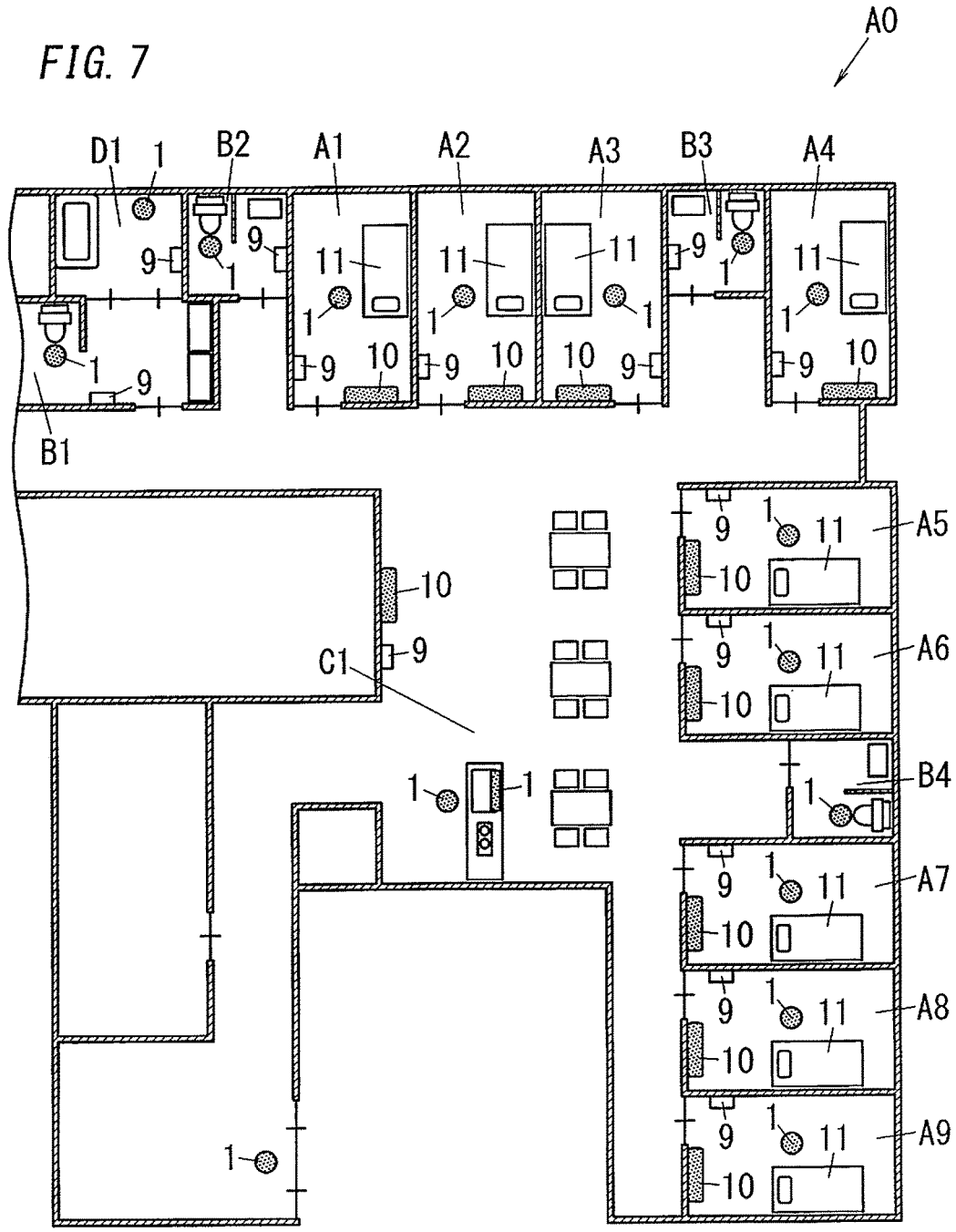
FIG. 7 is a floor plan of a share house in which a plurality of illumination devices according to Embodiment 2 are installed.

The life support system according to the present embodiment is preferably installed in a share-house A0 for the elderly, as shown in FIG. 7, for example. In the share-house A0, nine residential rooms A1 to A9, four lavatories B1 to B4, one dining kitchen C1, and a bathroom D1 are arranged in the first floor. A bed 11, an illumination device 1, and a reporting device 10 are installed in each of the residential rooms A1 to A9. Note that the analysis device 4 is installed in a control room, or the like.

The reporting devices 10 each include a communication function for communicating with the analysis device 4 wirelessly or by wire, a display device configured to display information that is received from the analysis device 4 using the communication function, and the like, and are installed in walls of the residential rooms A1 to A9, for example. Such a reporting device 10 may be a tablet computer having a wireless communication function, for example.

Also, the illumination devices 1 (illumination fixtures 2) each including a brightness sensor unit 25 are installed in ceilings of the respective residential rooms A1 to A9, which are private areas of respective residents (persons). Furthermore, the illumination devices 1 each including a person detection sensor unit 24 are installed in ceilings or walls of the lavatories B1 to B4, the bathroom D1, the dining kitchen C1, and like, which are common areas. Note that the reporting device 10 is also installed in a wall of the dining kitchen C1.

Also, the reader-writers 9 are installed in walls of the private areas and common areas (including hallways, the entrance, and the like; the same applies hereinafter), as shown in FIG. 7. Note that the reader-writers 9 may be installed in the ceiling. Also, the reader-writer 9 may be built into the illumination device 1 (illumination fixture 2 or adapter 3).

The identification tag 7 is preferably attached to an article that is always carried, worn, or used by a person when the person moves, the article being a walking stick, glasses, a wheelchair, a wristband, or the like, for example.

The analysis device 4 receives, with the communication unit 42, detection results notified from the adapters 3 of the illumination devices 1 (or illumination devices 1) and location information (information constituted by the identification code, the ID of a reader-writer 9, and the time; the same applies hereinafter) notified from the reader-writers 9, and stores the received information in the storage unit 41.

For example, the analysis unit 40, upon receiving location information from a reader-writer 9 that is installed in the lavatory B1, determines that a person associated with the identification code of the location information is using the lavatory B1. That is, since the lavatories B1 to B4 are arranged in the common area, the analysis unit 40 of the analysis device 4 cannot specify the user (person) from the detection results of the illumination devices 1 that are installed in the lavatories B1 to B4. Accordingly, the reader-writers 9 are installed in common areas, and the reader-writers 9 transmit pieces of location information to the analysis device 4, and as a result the analysis unit 40 can specify persons who are using the lavatories B1 to B4, the bathroom D1, and the like. In other words, the analysis unit 40 can individually confirm the locations of a plurality of persons wherever they are in the private areas and the common areas.

Accordingly, the analysis unit 40 can derive a lifestyle pattern of each of the persons based on the detection results (wake-up time, bedtime, and the like) of the illumination devices 1 in the private areas, the detection results of the illumination devices 1 in the common areas, and the location information of the reader-writers 9 that are stored in the storage unit 41.

Furthermore, the analysis unit 40 is preferably configured to derive, for each person, a typical lifestyle pattern from an average value of the lifestyle patterns over a long period of time (one month to one year, for example), compare, for each person, the lifestyle pattern with the typical lifestyle pattern, and determine the well-being of each person.

Also, the analysis unit 40 is preferably configured to calculate a distance that a person moves in the share-house A0 by analyzing location information obtained from the reader-writers 9, and determine whether or not the person has done an appropriate amount of exercise (walking). The analysis unit 40 is preferably configured to, upon determining that the person has not done enough exercise, cause a reporting device 10 that is installed in the residential room (A2, for example) of the person to report (display) a message or the like prompting the person to do some exercise.

Incidentally, the analysis unit 40 can grasp, in real time, the use situations of the lavatories B1 to B4 and the bathroom D1 based on the detection results of the illumination devices 1 and the location information obtained from the reader-writers 9. The analysis unit 40 is preferably configured to report the use situation of the lavatories B1 to B4 and the bathroom D1 from the reporting devices 10 in the residential rooms A1 to A9. That is, as a result of the use situation of the lavatories B1 to B4 and the bathroom D1 being reported from the reporting devices 10, persons can stay in the residential rooms A1 to A9 until the lavatories B1 to B4 and the bathroom D1 become available. As a result, the load on the persons and carers who care the persons can be reduced.

The life support system according to the present embodiment preferably includes the identification tag 7 that is attached to an apparatus 72 (walking stick, wheelchair, or the like) used by a person, and the plurality of reader-writers 9 that are arranged in the living space (share-house A0). The identification tag 7 preferably includes the transmission unit (communication unit 71) configured to transmit a specific identification code to the plurality of reader-writers 9. The plurality of reader-writers 9 each is preferably configured to transmit the identification code received from the transmission unit (communication unit 71) of the identification tag 7 to the analysis device 4. The analysis device 4 is preferably configured to derive the lifestyle pattern of the person by analyzing the detection results received from the adapters 3 and the identification code received from the plurality of reader-writers 9.

The life support system according to the present embodiment can derive lifestyle patterns of a plurality of persons even in the case of being installed in a living space (share-house A0) including private areas that are used solely by respective persons and common areas shared by the persons.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

The invention claimed is:
1. A life support system comprising:
   a plurality of illumination devices arranged in a living space; and
   an analysis device configured to analyze behavior of a person who lives in the living space,
   each of the plurality of illumination devices comprising:
      an illumination fixture; and
      an adapter for wiring tool,
   the illumination fixture comprising:
      a light source;
      a lighting device configured to turn on the light source;
      a fixture body supporting the light source and the lighting device; and
      a connection unit connected to the adapter,
   the adapter comprising:
      a detection unit configured to detect an operating state of the illumination fixture;
      a communication unit configured to communicate with the analysis device; and
      a control unit configured to cause the communication unit to transmit a detection result of the detection unit to the analysis device,
   the analysis device being configured to derive a lifestyle pattern of the person by analyzing the detection result received from the adapter, and to store a typical lifestyle pattern of the person and determine a well-being of the person by comparing the typical lifestyle pattern of the person with the lifestyle pattern of the person derived from analysis of the detection result,
   the lifestyle pattern of the person being derived from the time of day and the number of times that the detection unit has detected the operating state of the illumination fixture, and
   the typical lifestyle of the person being derived from an average value of the lifestyle patterns of the person over a long period of time.
2. The life support system according to claim 1, comprising:
   an identification tag to be attached to an apparatus that is used by the person; and
   a plurality of reader-writers that are to be arranged in the living space,
   wherein the identification tag comprises a transmission unit configured to transmit a specific identification code to the plurality of reader-writers,
   wherein each of the plurality of reader-writers is configured to transmit the identification code that is received from the transmission unit of the identification tag to the analysis device, and
   wherein the analysis device is configured to derive the lifestyle pattern of the person by analyzing the detection result received from the adapter and the identification code received from the plurality of reader-writers.

* * * * *